(12) United States Patent
Stanley et al.

(10) Patent No.: US 10,532,198 B2
(45) Date of Patent: Jan. 14, 2020

(54) METHODS FOR MAKING PRECISION APPLICATORS

(71) Applicant: The Procter & Gamble Company, Cincinnati, OH (US)

(72) Inventors: Scott Kendyl Stanley, Mason, OH (US); Michael Sean Farrell, Terrace Park, OH (US); Andrew Paul Rapach, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 158 days.

(21) Appl. No.: 15/611,895

(22) Filed: Jun. 2, 2017

(65) Prior Publication Data

US 2017/0354805 A1 Dec. 14, 2017

Related U.S. Application Data

(60) Provisional application No. 62/347,191, filed on Jun. 8, 2016, provisional application No. 62/475,254, filed on Mar. 23, 2017.

(51) Int. Cl.
*A61M 35/00* (2006.01)
*A45D 34/04* (2006.01)
*A45D 44/00* (2006.01)
*B05D 1/02* (2006.01)

(52) U.S. Cl.
CPC ............ *A61M 35/00* (2013.01); *A45D 34/04* (2013.01); *A45D 44/002* (2013.01); *A45D 44/005* (2013.01); *A61M 35/003* (2013.01); *B05D 1/02* (2013.01); *A45D 2044/007* (2013.01); *A61M 2205/055* (2013.01); *A61M 2205/057* (2013.01); *A61M 2207/00* (2013.01); *A61M 2210/04* (2013.01); *A61M 2210/0606* (2013.01)

(58) Field of Classification Search
None
See application file for complete search history.

(56) References Cited

U.S. PATENT DOCUMENTS

| 2008/0053476 A1 | 3/2008 | Lahood |
| 2009/0280150 A1 | 11/2009 | Kamen |
| 2010/0191314 A1 | 7/2010 | Young |
| 2011/0123703 A1 | 5/2011 | Mohammadi |
| 2012/0192884 A1 | 8/2012 | Nasu et al. |

(Continued)

FOREIGN PATENT DOCUMENTS

| CN | 104385589 | 3/2015 |
| CN | 104721061 | 6/2015 |
| WO | WO2014142439 A1 | 9/2014 |

OTHER PUBLICATIONS

International Search Report and Written Opinion dated Sep. 15, 2017, U.S. Appl. No. 15/611,909, 12 pgs.

(Continued)

*Primary Examiner* — Shamim Ahmed
*Assistant Examiner* — Bradford M Gates
(74) *Attorney, Agent, or Firm* — Sarah M DeCristofaro

(57) ABSTRACT

A method for forming an applicator comprises steps of: creating a digital geometric representation of the structure, the target structure having a flatness ratio; forming the applicator using the digital geometric representation of the target structure, the applicator having a target structure contacting surface; and disposing an active agent upon the target structure contacting surface of the applicator.

19 Claims, 1 Drawing Sheet

(56) References Cited

U.S. PATENT DOCUMENTS

2014/0163445 A1   6/2014   Pallari et al.
2015/0250971 A1   9/2015   Bachelder et al.
2015/0366327 A1  12/2015   Lahood, Sr.
2017/0086566 A1   3/2017   Stanley et al.
2017/0354806 A1  12/2017   Stanley et al.
2019/0167961 A1   6/2019   Stanley

OTHER PUBLICATIONS

International Search Report and Written Opinion, U.S. Appl. No. 15/611,895, dated Sep. 19, 2017, 5 pgs.

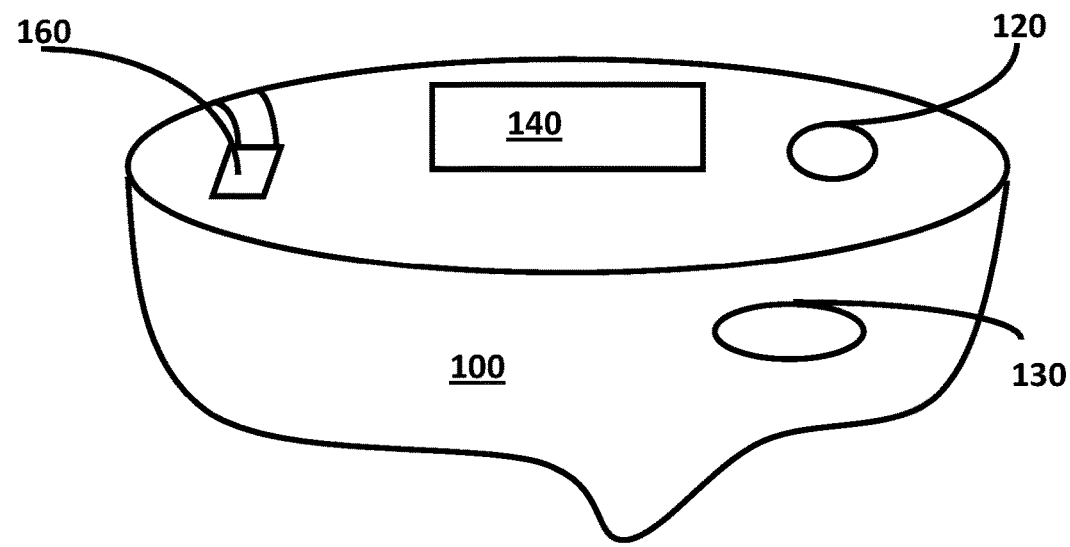
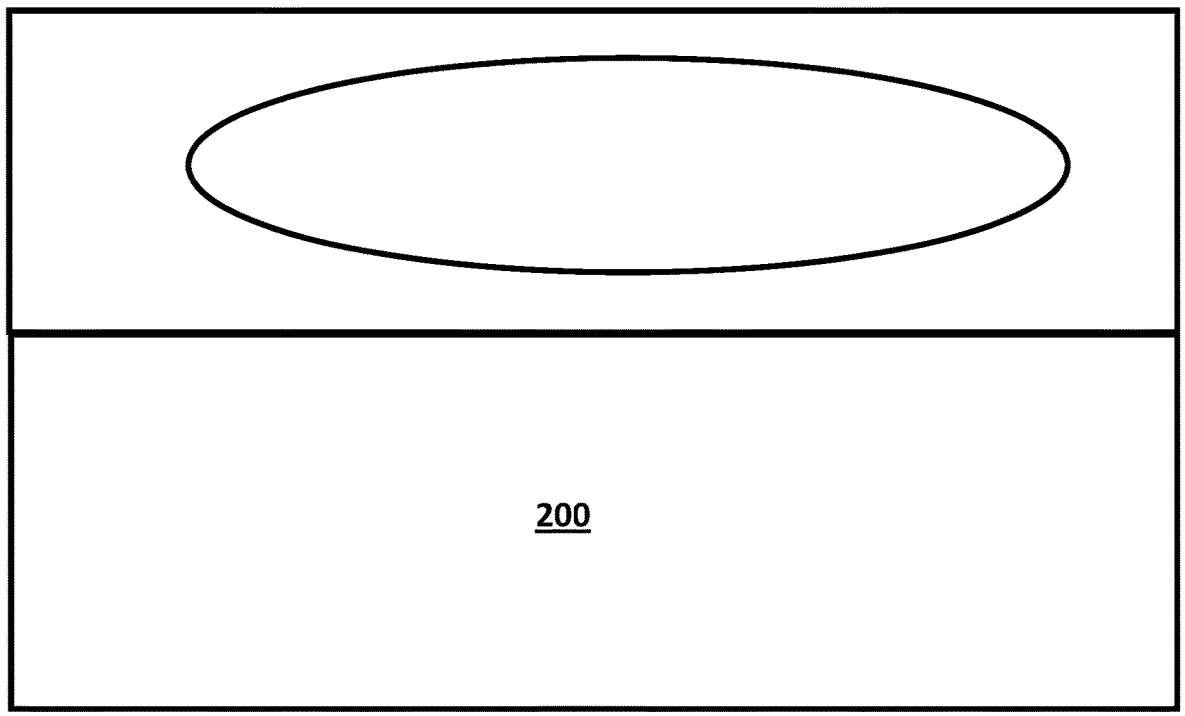

METHODS FOR MAKING PRECISION APPLICATORS

FIELD OF THE INVENTION

The invention relates to methods for making implements for applying active agents to a target structure. The invention relates particularly to methods for making implements custom fitted to precisely apply active agents to a target structure.

BACKGROUND OF THE INVENTION

Agents for affecting target structures are well known. Temperature affects may be induced by the application of hot or cold agents to the target. The appearance of a target may be affected by cosmetic and decorative agents. Electric current, voltages, and electric and magnetic fields may be applied to a target using local applicators. For biological targets, surface properties may be impacted by the use of topical application of moisturizers, medicaments and other treatment actives.

The effectiveness of the active agent may be impacted by the nature of the applicator available to facilitate the interaction of the active agent with the target structure. Typical applicators are less than precise with respect to their conformance to the target structure and the use of one-size, or a few sizes, fits all tends to compromise the actual performance of the active agent.

What is needed is a precision application implement adapted to the geometry of the target structure to yield an improved active agent performance and methods for making the applicator.

SUMMARY OF THE INVENTION

In one aspect, a method for forming an applicator comprises steps of: creating a digital geometric representation of the structure, the target structure having a flatness ratio; forming the applicator using the digital geometric representation of the target structure, the applicator having a target structure contacting surface; and disposing an active agent upon the target structure contacting surface of the applicator.

BRIEF DESCRIPTION OF THE DRAWINGS

FIGURE provides a schematic perspective view of an embodiment of the invention.

DETAILED DESCRIPTION OF THE INVENTION

In one aspect the applicator comprises a first structural element having a shape determined according to a digital geometric representation, or otherwise created digital geometric representation of a target structure. The first structural element may be flexible.

As used herein the term flexible means that the three-dimensional geometry of the element may be altered without any permanent deformation of the element's geometry.

As used herein, the term self-supporting means that the element retains a substantial portion of a defined three-dimensional shape without the aid of external support structures when resting on a horizontal surface in air.

As used herein, the term single-dose means an implement comprising sufficient active agents to afford a user only a single application of the active agent via the applicator.

As used herein, the term disposable refers to implements intended to be discarded after use rather than durable, or semi-durable implements intended for multiple uses either with or without the reapplication of an active agent.

In one embodiment, the applicator is a durable item suitable for washing by hand or in a dishwasher or clothing washing machine.

In one embodiment, the applicator of this invention includes an outer surface that may be dry and cleaner and easier for the consumer to handle. Due to the custom conformal fit to the target structure, for example a part of a human body, the applicator may be configured to have a low removal force. This may be accomplished through a combination of the conformal nature of the applicator and/or selected application of adhesive agents on controlled areas of the applicator, and/or other fastening means (for example, ear hooks, an elastic band, hook and loop straps, etc.). The three-dimensional scan of the target structure may be acquired using 3D scanners as are known in the art. An Artec Spider, available from the Artec Group, Palo Alto, Calif., is an exemplary 3D scanner. Using a smartphone such as an iphone 6 from Apple, Cupertino, Calif., and an app such as 123D Catch from Autodesk is another example of a process for creating a digital geometric representation of the target structure. The digital geometric representation of the target structure may be used as a whole or may be partitioned with only a portion of the total scan being used to define the shape of the structural element. Further, portions of the geometry derived from the scan may be removed or edited from the scan. For example, holes may be cut out from the scan data to aid with vision, breathing, or other body functions.

In one embodiment, a representation of a negative of at least a portion of the target structure may be created using known methods such as curable conforming mesh structures, heat-shapeable mesh structures, casting compounds such as plaster of Paris or clay. The completed negative of the target structure portion may then serve as the target for the geometric scan to provide the geometry of the target structure after appropriate processing to yield the surface common to the negative and the actual target structure itself. In one embodiment, the target surface scan may be accomplished by any known physical probe scanning method such as contact profiling using a stylus or an array of mechanically movable elements such as a pin art scanner.

In one embodiment, the target structure may be replicated as a physical representation, in whole or as a set of discrete parts. The replicated structure, or portion thereof, may be fabricated with ancillary portions (e.g. flanges) to facilitate the use of the fabrication as a forming mold upon which an applicator which is a negative of the target structure or portion may be cast or otherwise formed such as by thermoforming or vacuum forming a web or film to the shape of the negative.

The formed element is considered to have a geometry determined according to the digital geometric representation of the target structure. After the formed element has been created, the active agents determined from the diagnostic analysis may be printed or otherwise disposed upon the formed element(s).

In one embodiment, the forming mold may comprise at least one channel enabling the application of an active agent to the mold contacting surface of the applicator as or after the applicator is formed upon the mold but prior to removal of the applicator from the mold. The location of the channel (s) and the portions of the mold surface to which they extend may be general in nature or may be specifically located according to common target surface features or locations determined according to a diagnostic scan of the target surface.

In one embodiment, the geometry of the scanned target structure may be modified to add features to the formed element. As an example, the portions of a mask associated with a scanned subjects eyes, ears, mouth, or nostrils may be adapted in the geometry to facilitate the removal of these portions after the applicator is formed from the mold portions. Further modifications may include the addition of features for the purpose of securing the mask in place upon the target structure, such as hooks, flaps, and slots for attaching straps to the applicator. Pressure sensitive adhesives may be disposed upon the target structure contact surface of the applicator as a means of securing the applicator in place upon the structure.

In one embodiment, the portions of the target structure selected to correspond to portions of the applicator may be selected according to a function relationship between portions of the target structure. In such an embodiment, a user's jaw may be selected as a portion distinct from the remainder of the user's face such that a complete mask consisting of a jaw and the remainder may be fabricated and may include articulating hinged elements allowing the jaw of the completely assembled mask to articulate in a fashion mirroring the articulation of the user's jaw, when the mask is in use. Alternately, breaks, scores, programmed bending, hinging, or stretch elements may be added to any portion of the applicator.

In one embodiment, the portions of the replicated target structure may be connected by hinges or similar elements to yield a unitary mold upon which the applicator may be formed as described above. The formed applicator may subsequently have active agents applied and then be assembled to a final form ready for use in applying the active agents to the surface of the target structure.

The portions of the replicated target structure may be solid, or they may be formed as a hollow shell or as a shell having a honey-combed or similar internal network of struts supporting the external surface of the shell. Such a supported shell may be formed to reduce the amount of material necessary for forming the portions.

The respective portions of the formed elements may comprise flanges, slots and tabs, tongues and grooves, alignment indicators, and other such means to facilitate the combination of the portion associated elements into a combined whole associated with the target structure. The portions may be formed as a clamshell like structure comprising a living hinge over at least a portion of the overall element to enable the structure to be folded into a usable applicator in the shape of the target structure. The portions may be fixedly or releasably attached to each other suing adhesives, clips or other known means.

In one embodiment, the formed element may be inverted such that the surface intended for contact with the target structure becomes more easily accessed. As an example, a formed mask of a human face may be inverted such that the portion of the mask intended to contact the tip of the nose of the wearer of the mask, is outside rather than inside the mask. The now external surface may have one or more active agents applied using any appropriate technique such as spraying, dipping or printing, and the formed element may subsequently be re-inverted returning the target surface contact portion to the interior of the mask.

In one embodiment, one or more active agents may be applied to a sheet stock before it is formed over the external surface. The active agents may be applied in a uniform fashion or different types and or amounts of active agents pixel by pixel. For example, ink jet printing may be used to first print actives onto sheet stock. In addition, these printed actives may be printed in a pre-distorted pattern such that they are applied in a first location at a first thickness in order to achieve actives in a second desired location and thickness after the distortion that occurs in the forming process. These one or more active agents may be applied as pre-distorted to the sheet stock before forming such that the active agents will achieve the intended final location at the appropriate thickness on the final custom applicator element.

In some embodiments, sheet stock consists of a forming sheet stock of a material such as PET, LDPE, HDPE, PS, EVA foam or laminates and combinations and blends of these materials and other materials. In some embodiments forming operation is thermoforming, vacuum forming, or hydroforming. In some embodiments, nonwoven or woven substrate may be formed alone or in combination with another sheet stock. For example, sheet stock and nonwoven laminate with the nonwoven on the inner skin-contact side of the applicator.

Fabricating a replica of the structure may facilitate the printing or application of the active elements by enabling the creation of portions which afford the application apparatus easier access to the surfaces of the formed elements. Additionally, the portions when separate, may be, for example, flatter and easier to ship. As an example, a human face, fabricated as a single element, has a depth associated with the distance between the edge of the subjects face (i.e. at the ear) and the tip of the subject's nose. Alternatively, half of the same subjects face, formed upon a mold derived from a scan of the subject, has a depth associated with an imaginary plane passing through the tip of the nose and the edge of the subjects face. As another example, the depth of a hemisphere of radius r, is r but the depth of a section of that sphere, taken between two points spaced 90 degrees upon the surface of the sphere is only approximately 0.29 r. Applying actives to portions of an overall negative of a structure, is facilitated by effectively flattening the overall negative by parsing the structure and forming a set of elements which may be assembled after the appropriate application of active materials to the portions.

The flatness of a structure may also be considered in terms of a flatness ratio defined as the ratio of a projected area (projected from a top down normal to a horizontal supporting surface) to an actual printable surface area. In one example, a sheet of paper has a flatness of 1.0, whereas a full face scan of a Caucasian face has a flatness of about 0.6, whereas a half of the same face has a flatness of about 0.9. Flatness ratio closer to 1.0 is easier to spray uniformly and also one can achieve higher loading with fewer number of spray coating passes. Flatness ratio closer to 1.0 are easier to spray coat from a fixed Z height XY spray system that can be easier and less expensive to operate when compared to a spray system involving a multi axis arm (for the sprayer and or the surface) or any other type of conformal coating/printing system for applying materials to a non-flat surface.

In one embodiment, forming the structural element as a set of elements wherein each member of the set is flatter than the overall target structure, provides the benefits of enabling easier deposition of active agents to the structural elements as the set members are flatter, as well as the benefit of flattening the forming mold element portions associated with the structural elements. Flatter mold portions may require less material for their formation as well as less time to manufacture and less build space in an additive manufacturing system used for the fabrication. In one embodiment, the applicator may be fabricated from a transparent or translucent material to reduce the conspicuousness of the applicator upon the target structure. As an example, a transparent face mask applicator would attract significantly less attention to the user than a white or otherwise opaque mask when the user sought to wear the applicator in public such as during their daily commute.

In any embodiment, indicia, artwork, decorations of other visible elements may be added to the applicator using adhesives of by known printing techniques. The indicia etc may be added either before or after the structure is formed to its final useable shape.

The digital geometric representation data may be used without alteration, or the geometry of the representation may be altered, such as with a digital data processing system, to yield a new geometry derived, but differing, from the target structure geometry. The geometric differences may be imparted to the new geometry for the purpose of enabling the structural element to be used in the application of mechanical forces to the target structure. Mechanical devices may be added (e.g. levers, ratchets, moveable sections, and other known means) to impose forces upon the underlying target structure. The geometry may be altered to accommodate the reality that the physical applicator will have a non-zero thickness while also matching at least a portion of the geometry of the target surface.

In one embodiment, one or more target structure contacting portions of the applicator possesses conformal fit to the target structure, while the geometry of one or more non-contacting portions of the applicator may be fabricated to provide additional function and/or appearance. Functional features may be incorporated to improve the ability of the applicator by a consumer, manufacturer, distributor or retailer to handle, place, or otherwise manipulate the applicator. Exemplary functional features include one or more: grips, handles, toggles & strap receiving elements. Additional functional features may help maintain the position of the applicator in relation to the target structure. Such features may include elements such as an elastic band or tie receiving, attaching or anchoring element.

With respect to appearance features, a non-target-structure-contacting portion of the applicator, such an externally-facing surface, or side of the applicator, may be altered any of a number of ways. Rather than incorporating the geometry of the representation, it may be shaped in the design of a selection of available designs, or a custom design provided by the consumer, manufacturer, distributor or retailer. Exemplary designs or likenesses of people, characters, and drawings available commercially may be utilized. The likeness of Elvis Presley, Darth Vader, Christie Brinkley, Wonder Woman, Scooby-Doo or other likenesses, may be used. Furthermore, indicia or signal elements may be present, for example, a portion of the applicator may change color to indicate a suitable wearing time has been achieved. Alternately, directions such as massage points, massage directions or paths may be indicated with printed arrows or otherwise indicated. These may be coupled with structural features that assist in applying acupressure or acupuncture treatments.

In one embodiment, interface geometry may be added to the geometry derived from the representation for the purpose of enabling the representation-derived geometry to be merged with the externally facing element.

In one embodiment, the target structure may be a body portion of a mammal such as a human face, or other portion such as a limb, joint, or portion thereof of a mammal.

In one embodiment, the target structure may be associated with an applicator selected from a limited array of applicators as an alternative to a precise custom applicator. As an example, a scan, set of images, or other analysis of the target structure may be used to identify which element of a provided array of structures would be most suited to use for the application of an active to the target structure. The analysis could indicate that a particular applicator selected from the provided array of structures would provide sufficient precision in the application of the active to remove the need for a completely custom applicator.

In one embodiment, the representation, images, or other analysis may be used to determine a metric including facial size, surface area, perimeter, ear to ear distance, flatness of the face as determined using the normal distance between a vertical plane bisecting both subject ears and the tip of the subject's nose, or other target surface dimensional metrics. The range of the metric, or combination of metrics, may be used to define a limited set of applicators intended to be applicable to the entire range of metric values—e.g. small medium, large, x-large, covering the range. In embodiments where combinations of metrics are utilized, a multi-dimensional array of applicators may be configured for selecting an appropriate applicator according to the metrics of the particular user of subject.

The representation, images, or analysis may be used to determine dimensions associated with the location of features of the target surface. Using a face as an example, the location, size and shape of elements including the eyes, nostrils, or mouth may be determined according to their respective distances from a center line of the face. These locations, sizes and shapes may then be used to project those features upon an applicator selected from the array or set of potential applicators and openings for the selected features may then by cut through the applicator to provide eye holes, nostril or mouth openings.

In one embodiment, the use of the locations, sizes, and shapes of target surface elements may be used to provide a custom fit to applicators without providing applicators conformed to the three-dimensional geometry of the target surface. As an example, a flat facial mask may be customized by projecting the location of eyes, nostrils and mouth onto a flat facila mask substrate and creating openings associated with those features according to a scan or analysis of the target user's face in order to provide a low cost option with a relatively high degree of custom conformal fit to the user. By controlling for the difference between the 3-D scan data and the projection of that data onto the flat mask substrate, such that the created openings are disposed at the appropriate locations. Openings may be created using laser cutters or other means appropriate to cutting the applicator substrate. Additional scores or cuts may be added to the flat substrate to enhance the ability of the applicator to conform to the target surface. The outer perimeter of the applicator may be sized and cut according to the size and shape of the target surface intended for coverage.

The digital geometric representation, or image data may be further utilized as a diagnostic scanning tool by evaluating the data of the representation for geometric signatures identified as therapeutic indicators or triggers. The representation data may include visible light, variously polarized light, a particular narrow wavelength of light, ultra-violet, infrared, and/or ultra-sonic data associated with the representation of the target surface. The various data sets of the representation may be used as inputs to various diagnostic assessments for the purpose of identifying areas of opportunity for therapeutic treatment of the target structure.

As an example, a scan of a face may be analyzed to identify wrinkled skin, or the precursor geometric signatures known to indicate skin regions susceptible to or progressing toward a wrinkled condition.

The results of the diagnostic scan may be incorporated into the first structural element by way of indicia configured in the structure. The indicia may take the form of relative changes in the structure such as the texture, opacity, and/or color of the structural element at locations of opportunity identified from analysis of the diagnostic scan data.

The indicia may be used to indicate those portions of the surface of the structural element where a beneficial active material may be disposed such that placement of the structural element adjacent to the target structure may result in contact between the active material and the target structure.

In one embodiment, the location of the indicia may serve as deposition sites for active agents including therapeutic or cosmetic elements for the purpose of imparting therapeutic or cosmetic effects to the corresponding portions of the target surface. Such elements may be applied to the first structural element by hand, using a computer controlled robotic pick-and-place system, or by way of a three-dimensional printer. A 3Dn series, or tabletop series conformal dispensing system, available from nScrypt, Inc. of Orlando, Fla., is an exemplary printer for the deposition of the elements. For digitally instructed deposition systems of active agents to the first structural element, e.g. a three-dimensional printer, the actual indicia need not be printed or otherwise incorporated into the manufacture of the first structural element.

In one embodiment, the applicator and active agents are printed in the same process using a multiple extrusion head system, such as a Hyrel System 30 printer available from Hyrel LLC, of Norcross, Ga.

In one embodiment, active agent may be uniformly sprayed onto the applicator using any type of spray heads, such as from Nordson Corporation. These spray heads may be mounted onto XY scanning tables or multi-axis robotic arms to facilitate coating or operated in a hand held fashion. Electrospray, dip coating, electroplating, powder coating, anodizing, or other methods may be used as well to apply active agents or other materials to the structural element surface. Alternately, discrete zones, lines, or dots of active agent could be applied to the applicator surface using a material jetting approach, such as the Nordson Pico Jet valve.

In one embodiment, the active agents may be embedded or infused within the applicator material itself, such as Cupron Enhanced materials available from Cupron of Richmond, Va.

In one embodiment, the applicator may be fabricated as a system of multiple layers. In this embodiment, an inner, surface contact layer may be comprised of a first polymeric or thermoplastic or thermoset material selected for the purpose of holding and subsequently transferring an active agent to the surface. The inner layer's first material may lend itself to be more conformable to the target structure's response to pressure and/or surface topography displacement. For the applicator of multiple layers, a second polymeric or thermoplastic or thermoset material may be used to fabricate an outer layer intended to provide support for the inner layer including the option to provide much or all the flexible structure for the multiple layer applicator. The outer layer may also hold various therapeutic implements such as electrical elements, active agents which react exothermically to the addition of water, or thermal agents.

For the applicator of multiple layers, the first material and the second material may be the same material composition or may differ. For example the modulus, compressibility, and/or tackiness properties may singly be different or differ in any combination. Where the two materials differ: the outer material may be stiffer and/or possess a higher shore hardness value and/or a different color and/or a higher bending modulus than the first material of the inner layer. As another example the inner material may be softer and/or be more compressible and/or be tackier and/or be a different color and/or have a different Modulus of elasticity than the material of the outer layer.

The multiple layers may be fabricated concurrently or in a sequential fashion with one of the layers being fabricated prior to the other layer(s). Interactive sequential fabrication is contemplated wherein after a portion of one layer is fabricated, and then a portion of another layer is fabricated followed by a return to fabricate a different portion of the original one layer. The active agents may be deposited upon any layer at any time after the appropriate portion of the target layer is fabricated.

In one embodiment, the outer layers may include one or more functional or appearance features. In one example, the inner layer may be only partially, or not at all self-supporting, while the outer layer may be substantially or completely flexible.

In one embodiment of the applicator of multiple layers, the outer layer of the applicator may be selected from a limited array of outer layers into which a custom fit inner layer is fabricated. In one embodiment, the inner layer may be fabricated with an external surface shaped or containing features to permit it to attach or adhere to an outer layer of the applicator. In this embodiment, the outer layer may be selected from a limited array of pre-determined outer layers. As an example, at least a portion of the external surface shape of the inner layer conforms to at least one or more corresponding portions of the inner surface of the outer layer such that the two layers adhere to one another as is, or with the assistance of an adhesive, tacky resin, mechanical fastening, thermal lamination, or other means for at least releasably fastening the two layers together. As another example, mechanical fasteners or interlocks may be included with one attachment element affixed to, or comprising a portion of the external surface of the inner layer, and a corresponding mating attachment element affixed to, or comprising one or more corresponding portions of the inner surface of the outer layer. One example, of many known examples, is a snap fastener (also called press stud, popper, snap or tich) which comprises a pair of interlocking discs, made out of a metal or plastic, commonly used in place of buttons to fasten clothing and for similar purposes. The two interlocking (interference fit) discs make up a useful attachment system wherein the first disc is the one attachment element and the second disc is the mating attachment element.

The outer layer selected from the limited array of pre-determined outer layers may be reusable. A portion or the entirety of an inner layer may be removed or separated from the outer layer and discarded after use. Subsequently, at least a portion or a complete new inner layer may be affixed to the reusable outer layer. The new portion or complete inner layer may be derived from the original scan(s) or may be from a different scan.

Active agents may comprise active ingredients, carriers, chassis, emulsions, hydrogels, adhesives, process aides (such as thickeners, rheology modifiers, etc.). Active agents may further comprise a release layer to help active agents transfer from the applicator to the target surface. Active agents may include adhesive materials, active chemical agents, absorbent materials such as absorbent gel materials or absorbent foam materials placed according to either the diagnostic scan or relative to identifiable features. As an example, it may be desirable to dispose an absorbent foam material along cheekbones, brow or nose of a scanned user's facial mask, the disposition sites may be determined according to the geometry of the representation rather than according to the diagnostic scan of the user. Active agents may be in one or more physical forms, including but not limited to: foams, liquids, powders, films, fibers, creams, gels, hydrogels, encapsulated active agents, solids, combinations of these forms and other forms. Some examples of active agents include but are not limited to: moisturizer, anti-aging, anti-wrinkle, skin tone control, anti-irritation, sensates (e.g. menthol), heating or cooling chemistries, skin tightening, hair removal, hair regrowth, fungicide, antibacterial, antiviral, surfactants, cleaning agents, copper ion eluting (such as from Cupron of Richmond, Va.), antioxidants, vitamins, sunscreen, rejuvenation agents, wound healing agents, sebum management agents, astringents, exfoliates, anti-inflammatory, leave on, overnight, dry skin, itchy skin, cracked skin, peptides, acne, scar treatments, sore muscles, medicaments including pharmacological actives to treat disease states or other acute or chronic issues such as eczema, rashes, acne, cancer, cold sore, Psoriasis, Rosacea, Vitiligo, warts, diaper rash, Herpes, fungal nail infection, Actinic Keratosis, ulcers, corns, calluses, shingles, poison ivy, and insect bites. Further, the medicaments, including pharmacological actives, can go beyond topical effect and be designed for transdermal delivery of an active into the bloodstream or other internal tissue—such as in many therapies. Examples of therapies, both prescribed and unprescribed include: nicotine and hormone supplements.

Exemplary active agents for cosmetic changes to the target structure include: fingernail polish, toenail polish, deodorant, primer, lipstick, lip gloss, lip liner, lip plumper, lip balm, lip conditioner, lip primer, lip boosters, concealer, foundation, powder, rouge, blush, blusher, contour powder/creams, highlight, bronzer, mascara, eyeliner, and setting materials, scents, perfume or fragrance compositions (e.g. essential oils).

In one embodiment, the inclusion of one or more scents, perfume or fragrance compositions may be applied to the applicator for subsequent deposition to the target structure. However, a portion, or all, of the included one or more scents, perfume or fragrance compositions may act as experience agents. The experience agent provides a smell in the environs of the applicator when in use. For example, the smell provided bye a fragrance to suggest outdoor flower garden aroma may be desirable when applying cosmetic agents to the face of a consumer/wearer. Experiential agents need not necessarily be located on the target structure contact surface of the applicator. The agents may be located in a region not in contact with the target structure, such as on a non-contacting portion of the application side of the applicator or anywhere on any applicator side that is non-contacting to the target structure. The experience agent may be selected to accompany a selected appearance feature. In one embodiment, the indicia may comprise the active agent deposited upon the first structural element without alterations to the relative color or texture of the application site.

The active agents may be releasably deposited upon the first structural element such that the active agents will be substantially transferred from the first structural element to the corresponding locations of the target surface as or after the first structural element is brought into the proximity of, or actual contact with, the target structure.

In another example, a baseline scan may be made of a knee joint when there are no issues with the joint. Subsequent to the baseline scan, at a time when there is an issue with the joint, a subsequent scan may be made to identify changes in the geometry and surface temperature of the respective portions of the joint due to inflammation, or other causes. The representations may then be used for the purpose of generating a geometry associated with the joint and taking into consideration the baseline and current state of the joint. The geometry may be used to create a first structural element precisely matching the current state or modified from the current state using data from the baseline scan to create a modified geometry with the intention of selectively applying compression to the inflamed joint upon application.

The structural element may then serve as a target structure contact surface and may be combined with an outer shell element, or second structural element, having a geometry wherein there is an interface portion matched to a portion of the first structural element such that the outer shell and first structural element may be combined to form a hollow shell having an inner surface associated with the target surface and an interior volume derived from a therapeutic intent associated with the representation data for the joint. The combination may define a cavity between the elements. The location and volume of the cavity may be defined using data from the diagnostic scan.

In this example, the cavity of the combination shell may then be at least partially filled with a heating or cooling agent for the purpose of the precise application of relative heating or cooling of portions of the affected joint determined according to the representation data. The first structural and/or outer shell elements may be fabricated to include insulating portions, or to have structural features adapted for the subsequent installation of insulating elements to control those portions of the target structure and/or external environment subjected to the effects of the heating or cooling agents. In this manner, the exposure to the therapeutic temperature active agent may be precisely limited to only the portions of the target structure where such exposure is desired.

In one embodiment, the face may be scanned for geometry and also scanned for type, location, and amount of active elements. Then, a self supporting 3D mask may be printed with active elements on the inner surface for delivery to a consumer's face.

In another example, the face may be scanned for geometry and then the geometry processed to create a mechanical treatment plan for the face. The applicator, or series of applicators, can then through mechanical means alone and/or by using active elements apply forces to the face to hold the face into a new geometry, thus providing a face lift mask.

The first structural element and outer shell elements may be fabricated using either traditional machining methods, or the elements may be fabricated using additive manufacturing methods such as stereo-lithography or selective powder sintering techniques.

The elements or target surface mold or forming surface may be created using any polymer, thermoplastic or thermoset material. Examples include ABS, Nylon, polyolefin, polyester (e.g. PET, PLA), thermoplastics or elastomeric materials to impart an elastomeric nature to the elements. Photopolymer (SLA or continuous liquid interface printing, i.e. CLIP), sintered particles (e.g. SLS), binderjet particles, or any other methods of additive manufacturing may also be used. Metal, wood, ceramics, sand, wax, and other cast able, machine able or formable materials may also be used. The flexibility of the elements may also be altered by the inclusion of physical hinge elements in the design geometry of the elements. Hinges or other breaks in the applicator may be used to facilitate how the applicator is placed around a body part, such as around the elbow.

The target structure may be evaluated to define a level of flexibility desired in the first structural element and/or the combination of the first structural element and the outer shell element. The defined flexibility may subsequently be utilized to inform the element design in addition to the materials and fabrication technique selection for the elements in order to provide elements created with consideration for the flexibility or range of motion etc. of the underlying target structure.

The first structural element may comprise component elements enabling the application of electric current, voltage and/or electrical or magnetic fields to portions of the target structure. Electrodes, electrical coils and other necessary components may be disposed upon the surface of the element or embedded or printed within the element such that, with the addition of a power sources such as a battery, photovoltaic solar cell, line voltage or other electrical power source, the desired energy may be applied to the target.

The geometry of the applicator may be varied from that of the target to provide accu-pressure benefits via the applicator. Accu-puncture elements may be incorporated into the applicator directly or apertures associated with desired accu-puncture sites may be provided as part of the customized applicator. Indicia may be added to indicate beneficial massage sites.

In one embodiment, the applicator could have integrated electronic components to serve a variety of purposes. For example, the applicator could have integrated and printed electrical traces. These traces could connect a power source (such as a coin cell battery, printed battery, fuel cell, plug to the wall, or other power source) to actuators, sensors, or energy emitters. Example of actuators and energy emitters include LEDs, vibration sources, actuators to locally create a displacement to apply pressure, massage elements, thermoelectric heating and cooling elements, and electromagnets. The applicator may include structures enabling the attachment of such power sources and energy emitters as well.

In one embodiment, the integrated electronic components may be integrated into the outer layer and/or the inner layer of the applicator of multiple layers. Further, integrated electronic components may provide an experience function while using the applicator. Examples include connectivity to smartphone or audio devices such that music may be played using audio speaker elements integrated into a facial applicator mask during applicator use. As another example, they may include transmission elements, connection to or parts of or a complete virtual reality system. For the example of a facial treatment applicator (e.g. a mask) the wearer can enjoy virtual reality content during the use of the applicator.

In one embodiment, the applicator may be provided as part of a consumer product kit. The kit may comprise the applicator element, or elements, and one or more active agents. The active agents may be predisposed upon the first structural element, or may be provided in a form suitable for application to the structural element by the consumer/user of the kit elements. The kit may further include a key (map) indicating the points of deposition for the active agent upon the surface of the structural element according to indicia, or as an alternative to the indicia.

The elements of the kit may be provided in a plurality of ways. In one embodiment, the structural element and active agent may be prepared, frozen, and provided in combination as a frozen article to be applied frozen, or to be thawed and used. In one embodiment, the structural element and active agent may be combined and sealed to shield the active agent from environmental effects. The structural element and active may be provided enclosed in a sealed pouch, or the perimeter of the structural element may be adhered to a film element to enclose the active agent within a chamber shielded from the external environment.

As shown in the FIGURE: a kit 1000 comprises a first structural element 100. The first structural element 100, comprises indicia, 120, an active agent 130, an insulating element 140 and an electrical element 160. The kit 1000 further comprises a second structural element 200 configured to receive the first structural element resulting in the creation of a cavity (not shown) between the first and second structural elements.

For both the structural elements which are 3D printed, and the flexible elements which are formed upon molds which were 3D printed, the product/applicator may include various indicia formed as part of the manufacturing of the product. Such indicia may include brand logos or names, as well as the date of the representation, the time and date of manufacture, a serialized ID number, the active agents applied to the mask, a product expiration, useful life indicator or best if used by date derived according to the date of manufacture and the applied chemical agents.

In one embodiment, the created elements may be provided in packaging customized to better preserve the integrity of the product offering. In one embodiment, the package may comprise a polymeric film which in turn has been ring-rolled, gusseted, or otherwise geometrically altered such as is described in U.S. Pat. No. 5,366,782. Such geometric alteration impart elasticity to the film enabling the package to achieve a high degree of conformity to enclosed products across a wide range of actual product sizes, thereby minimizing the enclosed volume and any quantity of controlled atmosphere which may be used to further stabilize and protect the product. In some embodiments, the package may include a film or barrier film and or a carton or rigid sleeve and one or more elements to affix or align the applicator to a rigid element inside the flexible film.

The volume of the package may be pressurized and may comprise air or a specifically selected gas (e.g. argon, nitrogen) to preserve the product and protect the product by providing a degree of structural integrity by the pressurization of the package.

In one embodiment, the package comprises a custom shaped tray or support. In one embodiment, the package comprises release liner either in flat sheet, cut and or folded sheet, or partially or entirely formed into a custom shape.

A range of packages may be provided such that a higher degree of tailoring of the package to the product may be achieved. A range such as small, medium, and large may be provided separate from or in conjunction with the custom sizing features described above.

The package may comprise any known packaging materials such as wood, glass, polymer materials, foils, laminates, paper materials and other materials as are known in the art. In one embodiment, the package may comprise traditional boxes, films, sachets, bags, cans, and other know package forms. The package exterior may include indicia associated with brands, materials and other information associated with the product as well as network locations where more information associated with the product may be found. The packaging material may be a flexible pouch where a mask or mask portion is contained within. The pouch would have the necessary barrier properties to maintain the target shelf life, moisture levels, and integrity of the active agents and the applicator. The pouch may or may not be gusseted with one or more gussets. The pouch may further have an insert. The insert may be a single stiff sheet. The insert may be custom fit to the applicator according to the digital geometric representation. The insert may be a U shaped insert to create a fixed volume within the flexible pouch. The pouch may be inflated or held at a fixed volume through air trapping to maintain a fixed volume. The insert may be box with 6 faces, 5 faces, 4 faces, 3 faces, or 2 faces. The insert may have attachment points for the applicator to align and hold the applicator in place during shipment. The attachment points may be posts, fasteners, removable adhesive, or any other such attachments. The pouch may have transparent regions or any type of print, reverse print, metallization, or other coatings and decoration technologies.

The product may comprise stand-offs attached to, or separate from, the product itself to facilitate maintaining space between the package walls and the product, as well as to facilitate the stacking of a plurality of packaged products.

The packaged product may include space filling materials disposed between the surfaces of the product and the interior surfaces of the package to provide space and protection for the product as it is enclosed in the package.

The products may include extraneous flanges or other structures for the purpose of enabling the nesting or stacking of a multitude of products within a single package while maintaining the integrity of applied active materials. Release liners of silicone or wax coated sheets may be disposed between stacked products to facilitate separation of the products.

The data from scanning the target structure used previously increasing the product/formed element(s), may be further used as an input to creating a custom package for the product wherein the shape of the package is also associated with the shape of the target surface and the product. Such a custom package could be manufactured using a mold and known vacuum and thermo forming processes. In one embodiment, bar codes may be used to associate and enable the tracking and coordinated fabrication of products and packages The package may be hermetically sealed and may also comprise a transparent or translucent portion to enable viewing of the product enclosed within the sealed package. The sealed package may comprise a pre-determined atmosphere as described above. The sealed package may include indicia providing information related to the recipient, the date of manufacture, the shipping destination and other relevant information.

The applicator may be acquired by the user via a retail shopping experience. That experience may include steps of: scanning the subject target structure, or providing a scan of the structure, such as a scan using a Microsoft Kinect®, or providing data from a software scan created from multiple subject photographs, or providing data from a CT or MRI scan of the subject target, the representation data may include information for the purpose of completing a diagnostic evaluation of the target surface in terms of the absorption or reflectance of particular electromagnetic radiation frequencies, or the local appearance of discrete regions of the surface, or a evaluation of the DNA of the target user. The diagnostic scan may be used as the basis for determining specific locations upon the intended applicator for the disposition of active agents for the purpose of addressing needs identified in the diagnostic evaluation. A consultation with the user may be undertaken to discuss and explain the active agent options available and the relationship between those options and the opportunities indicated by the diagnostic evaluation. The user may make selections based upon the evaluation and or the consultation. The user's selections may be provided to the fabrication location such that the active agents associated with the user's selections may be incorporated into the applicators fabricated as a result of the representation and subsequent selections. A test applicator may be fabricated as a part of the retail experience to enable the user to experience the fit of the proposed applicator as part of assisting the user in understanding the fit related benefits of the custom created applicator as opposed to a one size fits all applicator of a flat web applicator when applied to a typically non-flat target surface. Subsequent to the acquisition of scan data and user inputs, the applicators may be fabricated as described above, either at the retail location or remotely, and then provided to the user. The user may receive the applicators either by returning to the retail location or via a mail delivery service. The retail experience may include subsequent scans of the user to determine and demonstrate alterations in the target surface due to the use of the applicators and associated active agents. Additional applicators may be fabricated in association with the subsequent scans. The additional applicators may include revised applicator geometries as well as revised active agents and active agent deposition targeting due to changes in the target.

A. A method for forming an applicator, the method comprising steps of:
    a. creating a digital geometric representation of the structure, the target structure having a flatness ratio;
    b. forming the applicator using the digital geometric representation of the target structure, the applicator having a target structure contacting surface; and
    c. disposing an active agent upon the target structure contacting surface of the applicator.

B. The method according to paragraph A, wherein the step of: forming the applicator using the digital geometric representation of the target structure, the applicator having a target structure contacting surface comprises: creating a physical representation of at least a portion of the target structure according to the digital geometric representation; forming the applicator using the physical representation of the target structure, the applicator having a target structure contacting surface.

C. The method according to paragraph B, wherein the step of: creating a physical representation of at least a portion of the target structure according to the digital geometric representation, further comprises creating a set of physical representations corresponding to a set of portions of the digital geometric representation of the target structure.

D. The method according to any of paragraphs: B, or C, wherein the step of: creating a physical representation of at least a portion of the target structure according to the digital geometric representation, further comprises creating active agent deposition channels as part of the physical representation.

E. The method according to any of paragraphs: B, C, or D, wherein the step of forming the applicator comprises thermoforming at least a portion of the applicator using the physical representation of the target structure.

F. The method according to any of paragraphs: B, C, D, or E, wherein the step of: creating a physical representation of at least a portion of the target structure according to the digital geometric representation, further comprises creating a physical representations corresponding to an altered digital geometric representation of the target structure.

G. The method according to any of paragraphs: B, C, D, E, or F, wherein the step of: creating a physical representation of at least a portion of the target structure according to the digital geometric representation, further comprises creating a physical representation of at a portion of the target structure having a flatness ratio which is higher than the flatness ration of the target structure.

H. The method according to any of paragraphs: B, C, D, E, F, or G, further comprising the step of removing a portion of the formed applicator.

I. The method according to any of paragraphs: B, C, D, E, F, G, or H, further comprising the step of scanning the target structure to create a digital diagnostic scan of the target surface.

J. The method according to paragraph I, further comprising the step of disposing the active agent upon the applicator according to the digital diagnostic scan.

K. The method according to paragraph A, wherein the step of: forming the applicator using the digital geometric representation of the target structure, the applicator having a target structure contacting surface comprises: creating a physical representation of at least a portion of the negative of the target structure according to the digital geometric representation; the physical representation having a target structure contacting surface.

L. The method according to paragraph K, wherein the step of: creating a physical representation of at least a portion of the negative of the target structure according to the digital geometric representation, further comprises creating a set of physical representations corresponding to a set of portions of the negative of the target structure according to the digital geometric representation.

M. The method according to any of paragraphs: K, or L, wherein the step of: creating a physical representation of at least a portion of the negative of the target structure according to the digital geometric representation, further comprises creating active agent deposition indicia as part of the physical representation.

N. The method according to any of paragraphs: K, L, or M, wherein the step of: creating a physical representation of at least a portion of the negative of the target structure according to the digital geometric representation, further comprises creating a physical representations corresponding to an altered digital geometric representation of the target structure.

O. The method according to any of paragraphs: K, L, M, or N, wherein the step of: creating a physical representation of at least a portion of the negative of the target structure according to the digital geometric representation, further comprises creating a physical representation of at a portion of the negative of the target structure having a flatness ratio which is higher than the flatness ratio of the target structure.

P. The method according to any of paragraphs: K, L, M, N, or O, further comprising the step of removing a portion of the created applicator.

Q. The method according to any of paragraphs: K, L, M, N, O, or P, further comprising the step of scanning the target structure to create a digital diagnostic scan of the target surface.

R. The method according to any of paragraphs: K, L, M, N, O, P, or Q, further comprising the step of disposing the active agent upon the applicator according to the digital diagnostic scan.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming an applicator, the method comprising steps of:
    creating a digital geometric representation of a target structure, the target structure having a flatness ratio;
    forming the applicator using the digital geometric representation of the target structure, the applicator having a target structure contacting surface; and
    disposing an active agent upon the target structure contacting surface of the applicator; and
    sizing the outer perimeter of the applicator to the target structure contacting surface.

2. The method according to claim 1, wherein the step of: forming the applicator using the digital geometric representation of the target structure, the applicator having a target structure contacting surface comprises: creating a physical representation of at least a portion of the target structure according to the digital geometric representation; forming the applicator using the physical representation of the target structure, the applicator having a target structure contacting surface.

3. The method according to claim 2, wherein the step of: creating a physical representation of at least a portion of the target structure according to the digital geometric representation, further comprises creating a set of physical representations corresponding to a set of portions of the digital geometric representation of the target structure.

4. The method according to claim 2, wherein the step of: creating a physical representation of at least a portion of the target structure according to the digital geometric representation, further comprises creating active agent deposition channels as part of the physical representation.

5. The method according to claim 2, wherein the step of forming the applicator comprises thermoforming at least a portion of the applicator using the physical representation of the target structure.

6. The method according to claim 2, wherein the step of: creating a physical representation of at least a portion of the target structure according to the digital geometric representation, further comprises creating a physical representations corresponding to an altered digital geometric representation of the target structure.

7. The method according to claim 2, wherein the step of: creating a physical representation of at least a portion of the target structure according to the digital geometric representation, further comprises creating a physical representation of at a portion of the target structure having a flatness ratio which is higher than the flatness ration of the target structure.

8. The method according to claim 2, further comprising the step of removing a portion of the formed applicator.

9. The method according to claim 2 further comprising the step of creating a digital diagnostic scan of the target structure.

10. The method according to claim 9, further comprising the step of disposing the active agent upon the applicator according to the digital diagnostic scan.

11. The method according to claim 1, wherein the step of: forming the applicator using the digital geometric representation of the target structure, the applicator having a target structure contacting surface comprises: creating a physical representation of at least a portion of the negative of the target structure according to the digital geometric representation; the physical representation having a target structure contacting surface.

12. The method according to claim 11, wherein the step of: creating a physical representation of at least a portion of the negative of the target structure according to the digital geometric representation, further comprises creating a set of physical representations corresponding to a set of portions of the negative of the target structure according to the digital geometric representation.

13. The method according to claim 11, wherein the step of: creating a physical representation of at least a portion of the negative of the target structure according to the digital geometric representation, further comprises creating active agent deposition indicia as part of the physical representation.

14. The method according to claim 11, wherein the step of: creating a physical representation of at least a portion of the negative of the target structure according to the digital geometric representation, further comprises creating a physical representations corresponding to an altered digital geometric representation of the target structure.

15. The method according to claim 11, wherein the step of: creating a physical representation of at least a portion of the negative of the target structure according to the digital geometric representation, further comprises creating a physical representation of at a portion of the negative of the target structure having a flatness ratio which is higher than the flatness ratio of the target structure.

16. The method according to claim 11, further comprising the step of removing a portion of the created applicator.

17. The method according to claim 11 further comprising the step of creating a digital diagnostic scan of the target structure.

18. The method according to claim 17, further comprising the step of disposing the active agent upon the applicator according to the digital diagnostic scan.

19. A method for forming an applicator, the method comprising steps of:
    creating a digital geometric representation of a target structure;
    forming the applicator using the digital geometric representation of the target structure, the applicator having a target structure contacting surface; and
    disposing an active agent upon the target structure contacting surface of the applicator; and
    sizing the outer perimeter of the applicator to the target structure contacting surface.

* * * * *